(12) United States Patent
Steube et al.

(10) Patent No.: US 6,638,251 B2
(45) Date of Patent: *Oct. 28, 2003

(54) THORACENTESIS DEVICE WITH HYPER-SENSITIVE DETECTION MECHANISM

(75) Inventors: Gregory Alan Steube, St. Charles, MO (US); Alan Ranford, Creve Couer, MO (US); Ronald Lloyd, Deland, FL (US)

(73) Assignee: Sherwood Services AG, Schaffhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/200,716

(22) Filed: Jul. 22, 2002

(65) Prior Publication Data

US 2002/0188254 A1 Dec. 12, 2002

Related U.S. Application Data

(63) Continuation of application No. 09/548,046, filed on Apr. 12, 2000, now Pat. No. 6,447,483.

(51) Int. Cl.[7] .............................................. A61M 5/178
(52) U.S. Cl. ................................... 604/158; 604/164.12
(58) Field of Search ................................. 604/158, 543, 604/164.12, 164.01, 264, 540, 541

(56) References Cited

U.S. PATENT DOCUMENTS

| | | |
|---|---|---|
| 5,139,485 A | 8/1992 | Smith et al. |
| 6,447,483 B1 * | 9/2002 | Steube et al. ............... 604/158 |

* cited by examiner

Primary Examiner—Edward K. Look
Assistant Examiner—Kimya N McCoy
(74) Attorney, Agent, or Firm—Ari M. Bai; Greensfelder, Hemker & Gale, P.C.

(57) ABSTRACT

A thoracentesis device having a hypersensitive dual spring indication mechanism for visually alerting the user of any contact to internal body organs by the blunt tip distal end of the device once the it as been inserted inside a patient's body. The thoracentesis device includes a handle and an outer needle fixedly attached thereto having a sharp distal end for penetrating a chest cavity wall and a conduit that is in communication with a cavity defined inside the handle. A dual spring-loaded inner needle is slidably disposed inside the conduit of the outer needle with the inner needle being operably is associated with a large spring that imparts a sufficient distal spring force to fully extend the blunt tip distal end of the inner needle beyond the sharp distal end of the outer needle and a small spring for imparting a smaller spring force thereto.

23 Claims, 5 Drawing Sheets

B-B VIEW

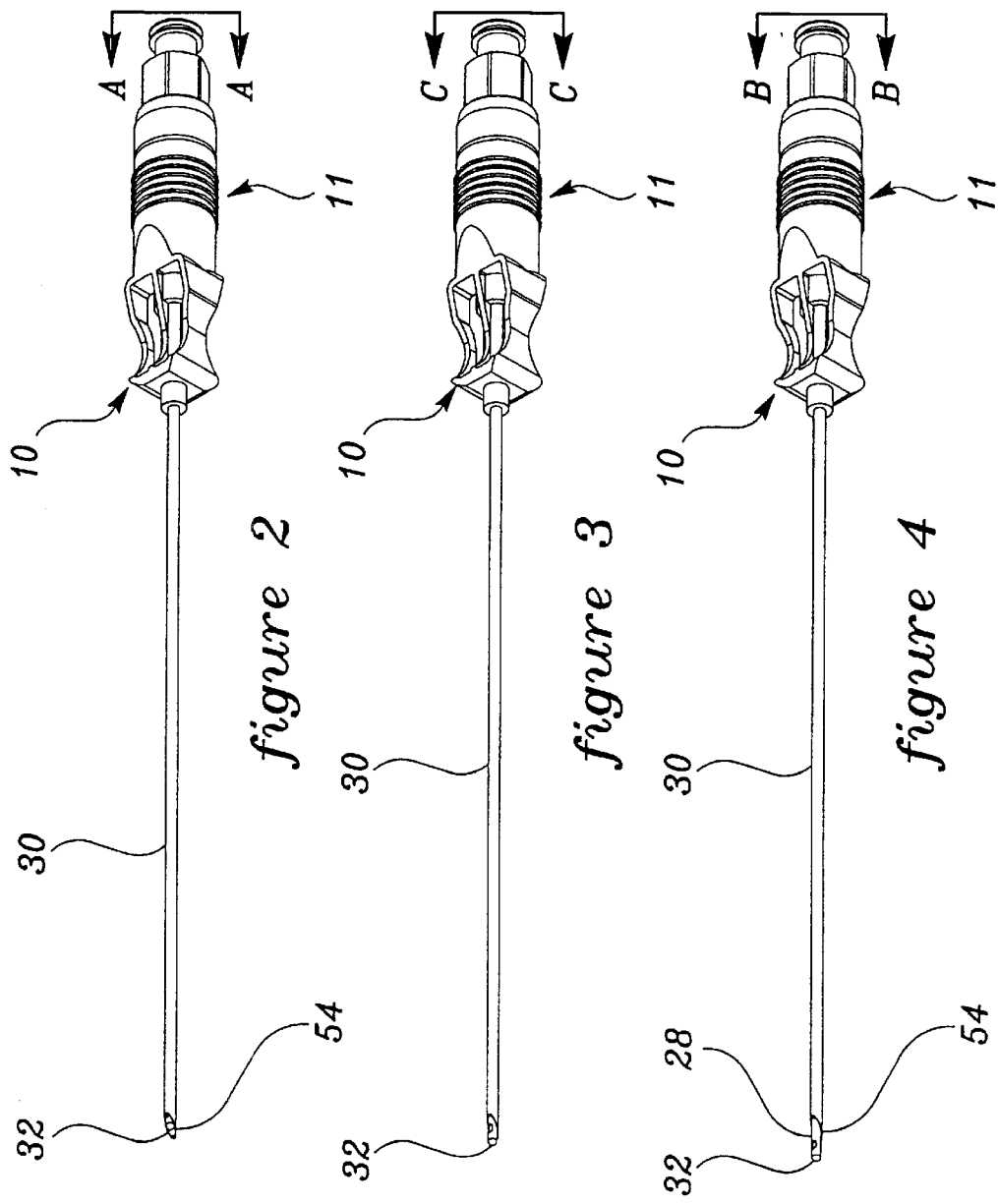

B-B VIEW

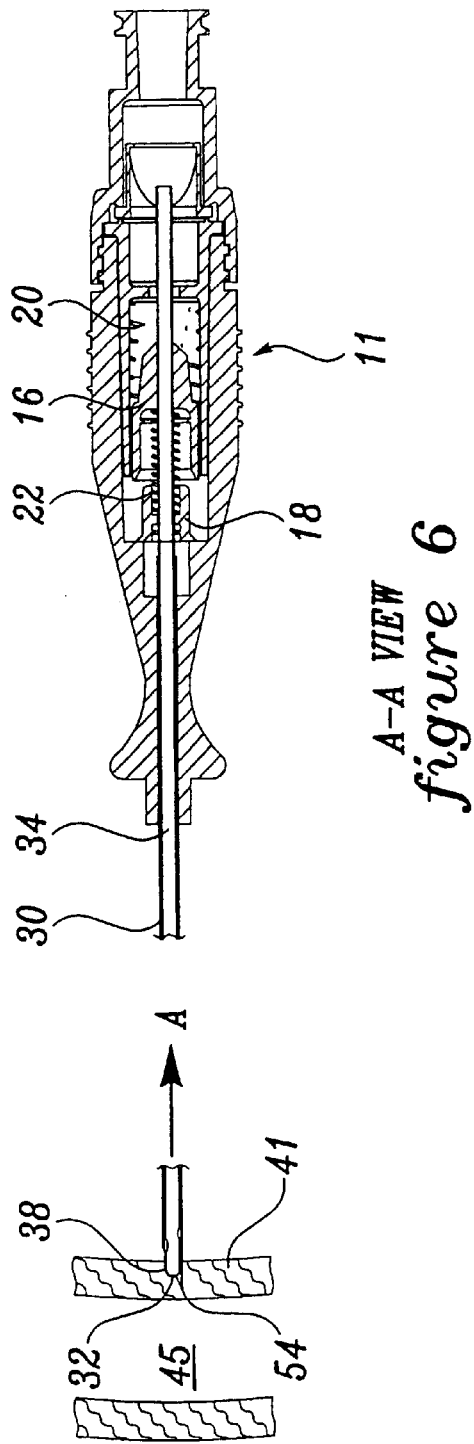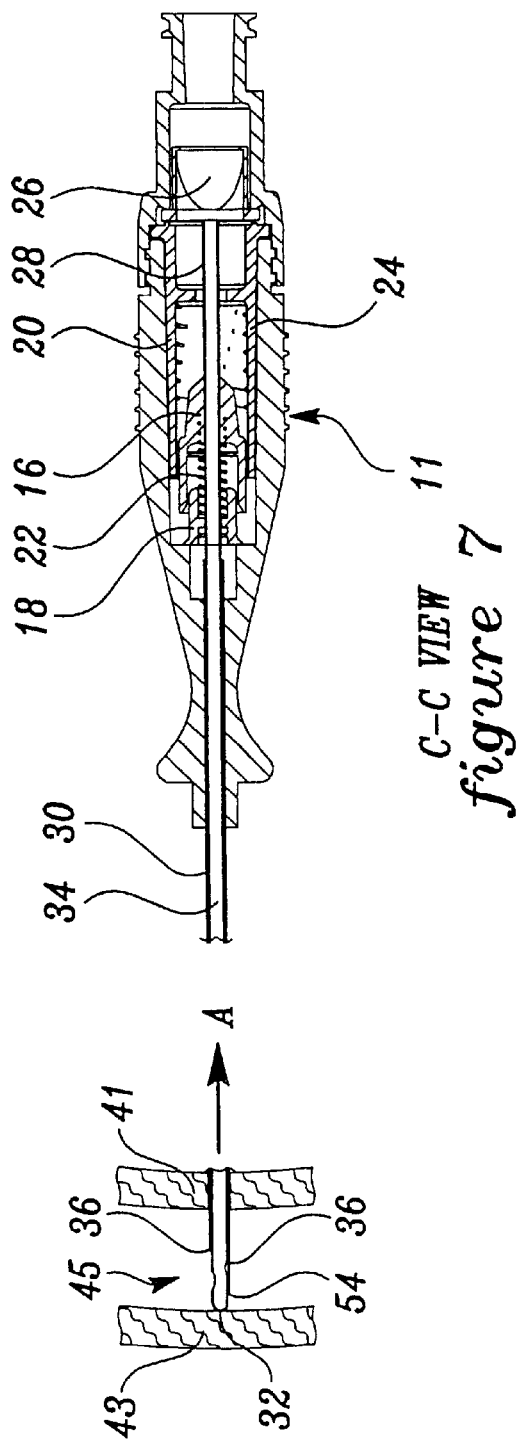

THORACENTESIS DEVICE WITH HYPER-SENSITIVE DETECTION MECHANISM

CROSS REFERENCE OF RELATED APPLICATIONS

This is a continuation of application Ser. No. 09/548,046 filed Apr. 12, 2000 now U.S. Pat. No. 6,447,483.

BACKGROUND OF THE INVENTION

1. Field of the Invention

The present invention relates to a medical device for performing thoracentesis, and more particularly to a thoracentesis device which is used for the removal of fluid from the pleural cavity. More specifically, the present invention relates to a thoracentesis device having a hypersensitive dual spring detection mechanism that greatly reduces the possibility of lung puncture or laceration by the device during thoracentesis.

2. Prior Art

Thoracentesis involves the removal or evacuation of fluid from the pleural cavity between the lungs and the chest wall of a patient who has sustained some kind of trauma to the pleural cavity area. Evacuation of fluid from the pleural cavity is a necessary procedure in order to allow the lungs to expand properly and promote proper convalescence. During a prior art thoracentesis procedure, a user makes an incision through the chest wall and inserts a catheter or other tubular member through the incision and into the pleural cavity. The proximal end of the catheter is then connected to a negative pressure source, e.g. luer tip syringe, and fluid which includes blood, air and other body secretions may be evacuated from the pleural cavity through the catheter by operation of the syringe.

Medical devices used to remove fluid from the pleural cavity during a thoracentesis procedure are well known in the art. A typical prior art device for performing thoracentesis is disclosed in U.S. Pat. No. 4,447,235 to Clarke entitled "Thoracentesis Device" which discloses a flexible catheter having a distal end and a proximal end, a means defining an elongated conduit connected to the proximal end of the catheter and in line therewith, and a hollow needle having a sharpened distal end adapted to penetrate the chest cavity. However, the drawback of the Clarke device is that an inadvertent puncture of an internal body organ by the sharpened distal end of the catheter could possibly occur during insertion of the device through the chest wall since there is no provision for indicating whether the sharp distal end of the device has made contact with the lungs, or other body organ, once the sharpened distal end enters the pleural cavity.

Other medical devices, such as verress-type needle device, used for pneumoperitoneum also require a means for detecting whether the sharpened distal end of the device has made contact with an internal body organ when insufflating the abdominal cavity. A typical Verress-type needle device is disclosed in U.S. Pat. No. 5,256,148 to Smith et al., entitled "Verress Needle with Enhanced Acoustical Means" which shows a single spring-loaded, blunt tipped inner needle slidably contained within a larger diameter piercing outer needle fixedly attached to the handle of the device. In operation, the outer needle of the Verress-type needle device is used to penetrate completely through the abdominal and stomach walls and enter the stomach. As the outer needle penetrates the stomach, the resistance applied against the single spring loaded inner needle causes the inner needle to withdraw inside the conduit of the outer needle such that the sharp end of the outer needle is exposed and extends outwardly beyond the blunt tip inner needle. Once the outer needle completely penetrates the stomach wall and enters the stomach, the resistance against the end of the inner needle applied by the stomach wall is removed so that the single spring force applied to the inner needle causes the blunt tip distal end thereof to move forwardly to a fully extended position beyond the sharp distal end of the outer needle. The Smith et al. device is also provided with a detection means for visually indicating to the user whether the fully extended blunt tip distal end of the inner needle has made contact with an internal body organ after insertion into the stomach. The detection means of the Smith et al. device comprises a single spring arrangement wherein the proximal end of the inner needle disposed inside the housing of the device is spring loaded and operatively connected to a detection means such that a visual indication is given to the user that contact has been made by the blunt tip distal end of the inner needle. The detection means also features two opposite colored bands that are viewed through a window made in the handle of the device. One of the colored bands indicates that the blunt tip distal end of the inner needle is in a fully extended position outwardly beyond the sharp tip of the outer needle, thereby visually indicating to the user that the distal end of the device has not made physical contact with an internal body organ after entry into the stomach. The opposite colored band indicates that the blunt tip distal end of the inner needle has made contact with a body organ and has been retracted into the conduit of the outer needle so that the sharpened tip of the outer needle is exposed. These opposite colored bands provide a visual stimulus to the user as to whether contact is being made by the blunt tip distal end of the device with an internal body organ, thus inadvertent puncture or lacerations of other body organs can be prevented. However, the detection means of the Smith et al. device could be improved even further when applied to thoracentesis or other invasive procedures. The single spring arrangement used to visually indicate the position of the distal end of the device could be improved to provide enhanced detection sensitivity to indicate whether contact has been made with the lungs or other internal body organs.

Therefore, there appears a need in the art for a medical device which includes an indication means that provides improved sensitivity as to the position of the blunt tip distal end of the inner needle relative to the sharpened outer needle of the device.

OBJECTS AND SUMMARY OF THE INVENTION

In brief summary, the present invention overcomes and substantially alleviates the deficiencies in the prior art by providing a thoracentesis device having a hypersensitive dual spring detection mechanism that provides quick and immediate visual indication to the user of when the blunt tip distal end of the inner needle of the device has made contact with a body organ, thereby preventing puncture or laceration of the lung area during thoracentesis. The thoracentesis device of the present invention comprises an outer needle fixedly attached at its proximal end to a handle and a sharp distal end adapted for penetrating the chest wall of a patient. The sharp distal end of the outer needle includes an opening in communication with a first conduit formed along the longitudinal axis of the outer needle. Slidably disposed inside the first conduit is a smaller diameter inner needle having a spring-loaded proximal end slidably engaged inside the handle and a blunt tip distal end which, in its fully extended position, extends a short distance outwardly beyond the sharp distal end of the outer needle. A plurality of radial ports are formed around the blunt tip distal end of the inner needle with each port in communication with a second conduit that extends longitudinally through the inner needle and opens into a cavity formed inside the handle. The second conduit of the inner needle provides a means for evacuating fluid via a fluid pathway established through the second conduit and cavity of the thoracentesis device.

The blunt tip distal end of the inner needle is maintained in its fully extended position due to its operative engagement with a large spring housed in the handle which applies a distal spring force along the longitudinal axis of the inner needle. The inner needle is also operatively engaged with a small spring which applies a smaller proximal spring force in direct opposition to the distal spring force applied by the large spring. The large spring and a small spring form a part of the dual spring detection mechanism of the present invention which provides an immediate visual indication that the blunt tip distal end of the inner needle has made contact with an internal organ, such as the lungs, while the thoracentesis device is operating inside the pleural cavity of a patient. When properly assembled, the detection mechanism has a dual spring arrangement operatively connected to an indicator arrangement comprising positive and negative indicators. The positive indicator is attached to a portion of the blunt tip inner needle housed in the cavity of the handle so that longitudinal movement by the spring-loaded inner needle necessarily moves the positive indicator relative to the stationary negative indicator which is nested and hidden inside the positive indicator. A cavity is formed at the distal end of the positive indicator for housing and completely masking the negative indicator from view through the transparent housing of the handle when the inner needle is in a fully extended position.

The dual spring arrangement according to the present invention is designed so that the large spring is in a minimum compressed state and the small spring is in a maximum compressed state when the blunt tip distal end is maintained in its fully extended position. In operation, when the blunt tip distal end makes contact with a body organ, e.g. the lungs, after insertion of the thoracentesis device through the patient's chest wall, the proximal contact force applied by the lungs to the blunt tip distal end of the inner needle in combination with the proximal spring force generated by the small spring, more quickly overcomes the distal spring force applied by the large spring at a reduced organ contact force than that required of prior art single spring arrangements. In other words, the addition of the proximal spring applied by the small spring requires a much smaller contact force to be applied by the contacted organ in order to more quickly visually alert the user that the inner needle is being withdrawn and the sharp distal end of the outer needle is being exposed. As the combined proximal forces applied by the small spring and contacted body organ become greater than the single distal spring force applied by the large spring, the positive indicator is made to move relative to the stationary negative indicator which exposes the negative indicator to view from its nested position inside the positive indicator and visually alerts the user that contact has been made by the blunt tip distal end of the inner needle. Accordingly, the addition of a second spring provides added detection sensitivity to the slightest contact made by the blunt tip distal end of the inner needle which better avoids inadvertent punctures or lacerations by the sharp distal end of the outer needle.

It will be appreciated that the dual spring arrangement of the present invention provides enhanced detection sensitivity by the thoracentesis device to the slightest contact made by the blunt tip distal end of the inner needle with a body organ. In the absence of the small spring providing a counterforce against the large spring, a much greater contact force by the body organ against the blunt tip distal end would be required to detect and alert the user that an internal organ was contacted. This lessened sensitivity by the single spring detection mechanism could cause possible inadvertent puncture or laceration of the lung wall since the user would be unaware that the blunt tip distal end had made sufficient contact with the body organ and exposed the sharp distal end of the thoracentesis device to the body organ.

The thoracentesis device of the present invention further comprises a sleeve member disposed in the cavity of the handle. The sleeve member includes distal and proximal bores with the distal bore housing the large spring therein as well as a portion of the positive indicator. The sleeve member also includes an axial opening formed through an internal shoulder which communicates with both proximal and distal bores and establishes a fluid pathway which extends from the radial ports of the inner needle to an opening formed at the proximal end of the handle. The proximal bore communicates with a one-way valve for preventing the reflux of evacuated fluid back through the thoracentesis device. Finally, the opening may be connected to a negative pressure device, e.g. a luer-tipped syringe, for manually evacuating fluid from the pleural cavity and out through the thoracentesis device.

Accordingly, a primary object of the present invention is to provide a medical device which is operable to reduce the possibility of inadvertent puncture or laceration of the lung or other body organ by the device.

Another object of the present invention is to provide a hypersensitive detection means for quickly indicating contact of a body organ by the distal end of the medical device to the user.

A further object of the present invention is to provide a visual indication means that may be viewed at any angle through the handle of the medical device.

Another further object of the present invention is to provide a dual spring arrangement operatively connected to a visual indication means for enhanced detection of an internal body organ by the medical device.

These and other objects of the present invention are realized in the preferred embodiment of the present invention, described by way of example and not by way of limitation, which provides for a medical device having a hypersensitive detection means for indicating contact of the distal end of the device with a body organ.

Additional objects, advantages and novel features of the invention will be set forth in the description which follows, and will become apparent to those skilled in the art upon examination of the following more detailed description and drawings in which like elements of the invention are similarly numbered throughout.

BRIEF DESCRIPTION OF THE DRAWINGS

FIG. 2 is a perspective view of the thoracentesis device with the blunt tip distal end in the retracted position exposing the sharpened distal end according to the present invention;

FIG. 3 is a perspective view of the thoracentesis device with the blunt tip distal end in a partial retracted position according to the present invention;

FIG. 4 is a perspective view of the thoracentesis device with the blunt tip distal end in the fully extended position according to the present invention;

FIG. 6 is a cross-sectional view of FIG. 2 taken along line A—A in FIG. 2 with the blunt tip distal end in the retracted position and the sharpened distal end penetrating the chest wall according to the present invention;

FIG. 7 is a cross-sectional view taken along line C—C shown in FIG. 3 with the blunt tip distal end in the partial retracted position when in contact with the lung wall according to the present invention.

DETAILED DESCRIPTION OF THE INVENTION

Figure 1:
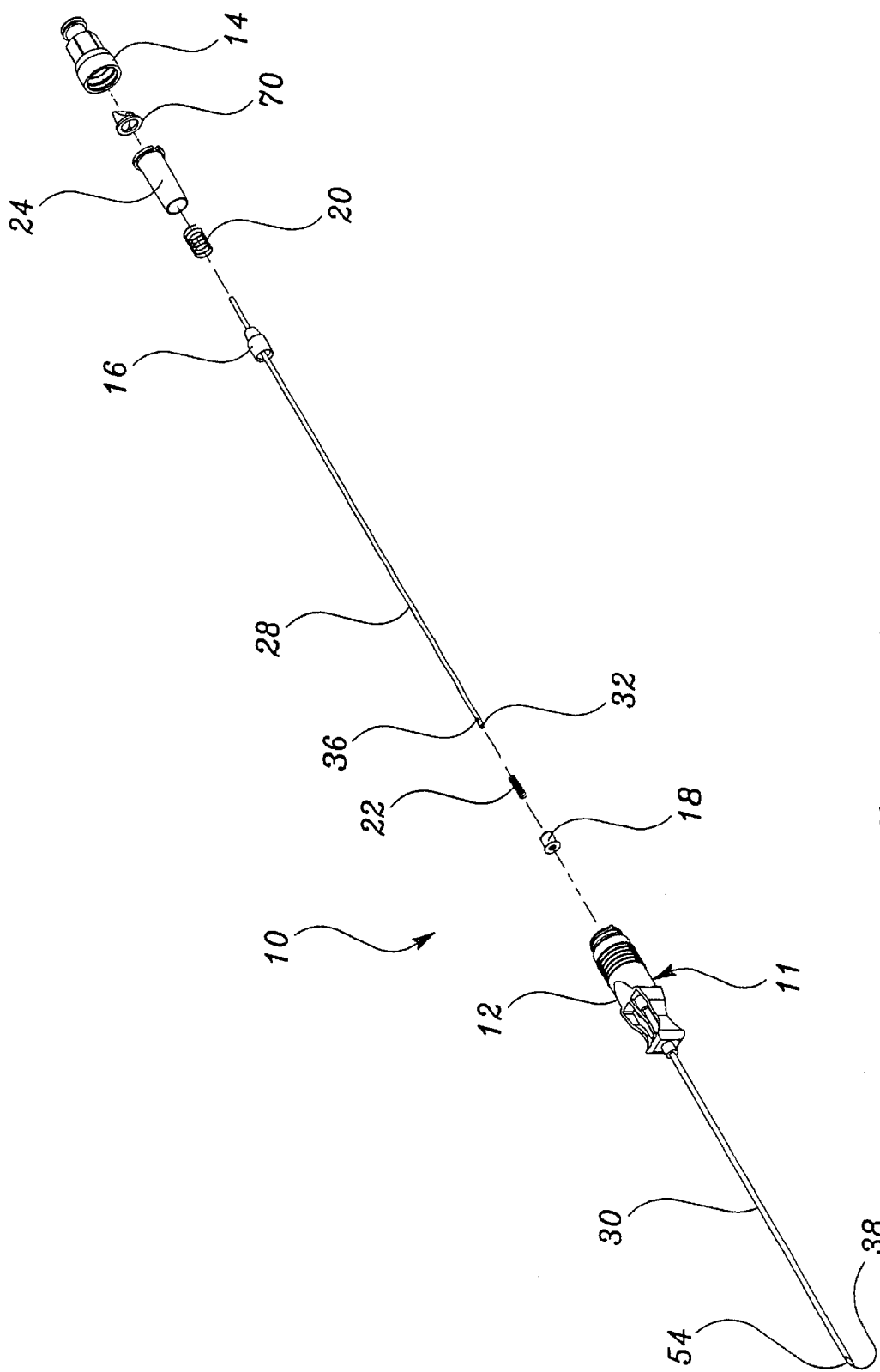
FIG. 1 is an exploded view of the thoracentesis device according to the present invention.
Figure 5:
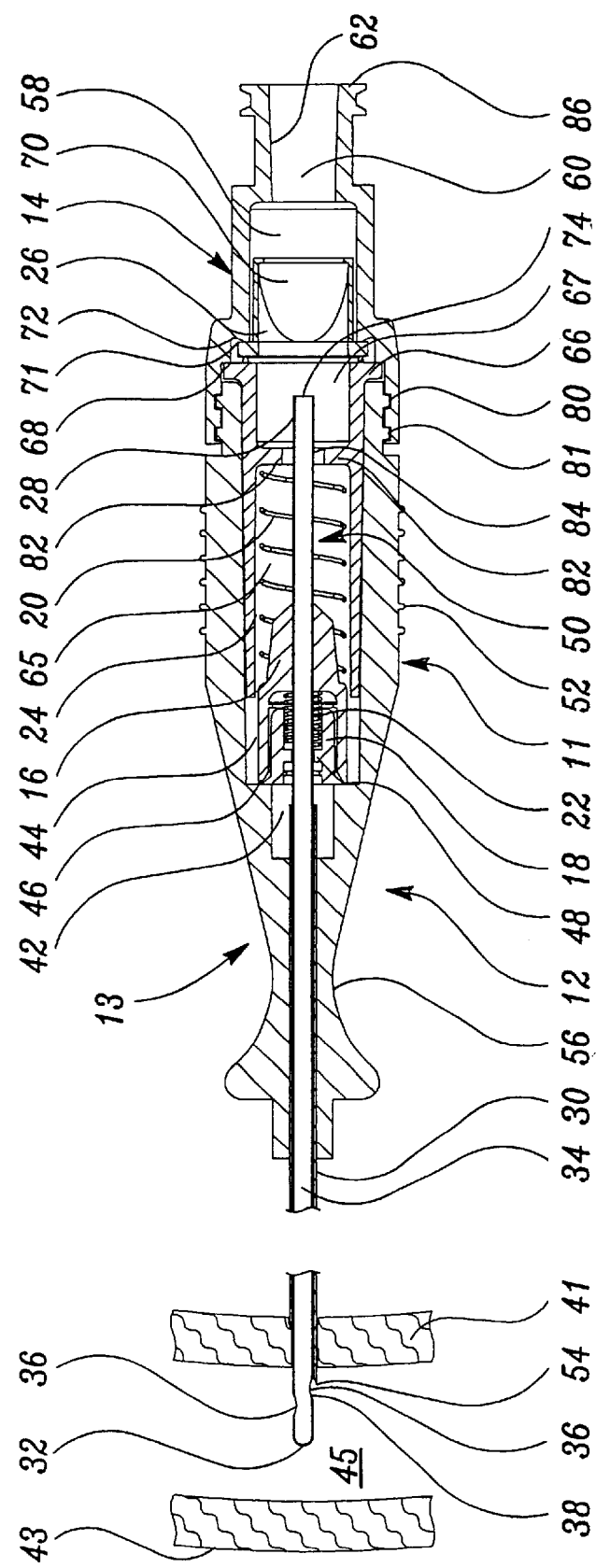
FIG. 5 is a cross-sectional view of the thoracentesis device taken along line B—B shown in FIG. 4 with the blunt tip distal end in the fully extended position inside the pleural cavity according to the present invention.

Referring to the drawings, the preferred embodiment of the thoracentesis device of the present invention is illustrated and generally indicated as 10 in FIG. 1. For ease of reference, distal shall refer to the end of the device farthest away from the user, while proximal shall refer to the end of the device closest to the user. Referring to FIGS. 1 and 5, thoracentesis device 10 comprises a handle 11 having a transparent hollow body 13 and a hollow outer needle 30 fixedly attached to handle 11.

As shown specifically in FIG. 5, handle 11 comprises a front housing 12 attachable to a rear housing 14 which defines a cavity 50 within handle 11. The front housing 12 includes an external threaded portion 80 which mates with a corresponding internal threaded portion 81 formed along the exterior surface of rear housing 14 by rotating either housing 12,14 relative to the other until a sealing engagement is obtained between threaded portions 80, 81. As further shown, front housing 12 forms an annular chamber 42 which communicates with a larger annular chamber 44. The outer surface of handle 11 forms a finger portion 56 at the distal portion thereof adapted to be gripped between the user's thumb and forefinger during operation of thoracentesis device 10. A gripping portion 52 is also formed along the outer surface of handle 11 at its middle portion for engagement by the palm of the user.

Outer needle 30 defines a longitudinal inner conduit 34 which extends the entire length of outer needle 30 and communicates with a distal opening 38 formed at the distal end of thoracentesis device 10. Outer needle 30 further includes a sharpened distal end 54 which is adapted to penetrate through a chest wall 41 of a patient and is formed adjacent the distal opening 38. Referring to FIG. 7, slidably disposed along conduit 34 and longitudinally aligned with outer needle 30 is a spring-loaded inner needle 28. The proximal end of inner needle 28 is spring-loaded by virtue of its operative connection to a large spring 20 disposed inside handle 11, while the distal end of inner needle 28 defines a blunt tip distal end 32 with a plurality of radial ports 36 formed adjacent end 32 which communicate with conduit 34. The blunt tip distal end 32 provides a safe blunt surface for contacting the lung wall 43 or other body organ without penetrating or lacerating the tissue. Referring to FIGS. 4 and 5, when properly assembled large spring 20 imparts a spring force in the distal direction to inner needle 28 sufficient to place the blunt tip distal end 32 of needle 28 in a fully extended position that extends beyond the sharpened distal end 54 of the outer needle 30.

In addition to large spring 20, thoracentesis device 10 further includes a small spring 22 which is slidably mounted around a portion of inner needle 28 housed in handle 11 and provides a smaller proximal spring force to inner needle 28 in direct opposition to the spring force applied by the large spring 20 in the distal direction. As shall be discussed in greater detail below, large spring 20 imparts a greater spring force than the spring force applied by the small spring 22 such that the blunt tip distal end 32 of inner needle 28 is maintained in its fully extended, non-contact position forward of the sharpened distal end 54. The large spring 20 and small spring 22 comprise a dual spring arrangement 90. The dual spring arrangement 90 is designed such that large spring 20 is in a minimum compressed state and small spring 22 is in a maximum compressed state when the blunt tip distal end 32 is maintained in the fully extended position. When the blunt tip distal end 32 contacts an internal body organ, the spring loaded inner needle 28 is moved in the proximal direction which forces the small spring 22 to uncompress and the large spring 20 to compress.

According to another aspect of the present invention, thoracentesis device 10 comprises positive and negative indicators 16 and 18 having respective contrasting colors for providing a visual stimulus to the user that the blunt tip distal end 32 has made contact with an internal body organ. Positive and negative indicators 16 and 18 are housed inside the transparent body of handle 11 and at least one of the indicators 16, 18 are visible to the user at all angles through handle 11. Referring to FIGS. 1 and 5, positive indicator 16 is fixedly attached along a portion of inner needle 28 housed inside handle 11 and is partially disposed inside a distal passage 65 of a hollow sleeve 24 which is slidably mounted along inner needle 28. Positive indicator 16 includes a chamber 46 which is adapted to nest negative indicator 18 therein when blunt tip distal end 32 is in the fully extended position. As further shown, negative indicator 18 is stationary and fixedly positioned inside cavity 50. As shall be explained in greater detail below, when blunt tip distal end 32 makes contact with a internal body organ inner needle 28 is forced backward such that positive indicator 16 moves relative to the stationary negative indicator 18 and unmasks indictor 18.

Sleeve 24 has a generally hollow tubular configuration and includes distal passage 65 and proximal passage 67 separated by an inner wall 82 interposed across the interior of sleeve 24. Inner wall 82 forms an axial opening 84 that slidably engages the proximal portion of inner needle 28 therethrough. To securely retain sleeve 24 inside handle 11, the end of proximal passage 67 defines an annular flange 66 for seating against inner shoulder 68 that sandwiches flange 66 between the front and rear portions 12, 14 handle 11, thereby fixedly maintaining sleeve 24 in a stationary position inside cavity 50. Handle 11 further includes a chamber 58 for housing a one-way valve 70 which provides a means of preventing the reflux of evacuated fluid back through thoracentesis device 10 as well as preventing atmospheric air from entering the pleural cavity during operation of device 10 through the chest wall 41. As further shown, one-way valve 70 includes an annular flange 71 formed adjacent one end thereof for anchoring valve 70 between sleeve 24 and an inner shoulder 72 formed along the interior surface of handle 11. Preferably, one-way valve 70 is a duck bill valve, although any valve which functions to prevent reflux of fluid being withdrawn in one direction, while also preventing atmospheric air from entering into the pleural cavity from the other direction, is felt to fall within the scope of the present invention.

Referring to FIGS. 2–7, the operation of thoracentesis device 10 will be discussed in greater detail. FIGS. 5–7 illustrate the sequence of the thoracentesis device 10 as the outer needle 30 penetrates the chest wall 41 of a patient. Referring specifically to FIG. 6, the user penetrates through the chest wall 41 of a patient by contacting the blunt tip distal end 32 of thoracentesis device 10 against wall 41 until the combined force generated by the resistance of chest wall 41 and the proximal spring force applied by small spring 22 to inner needle 28 overcomes the distal spring force similarly applied by the large spring 20. Referring to FIG. 7, as sufficient contact is made by the blunt tip distal end 32, distal end 32 is forced to withdraw backward in the proximal direction into conduit 34 as the sharpened distal end 54 of outer needle 30 is exposed and penetrates through the chest wall 41. Once the sharpened distal end 54 of thoracentesis device 10 completely penetrates the chest wall 41, distal end 54 enters the pleural cavity 45 of the patient.

As illustrated in FIG. 5, once the sharpened distal end 54 enters the pleural cavity 45, the resistance generated by chest wall 41 against distal end 54 ceases and the distal spring force applied by the large spring 20 overcomes the smaller proximal spring force applied by small spring 22. This forces the blunt tip distal end 32 forwardly out from conduit 34 such that tip 32 is placed in its original fully extended position beyond the sharpened distal end 54. In the fully extended position, blunt tip distal end 32 shields sharpened distal end 54 so that end 54 is prevented from lacerating the tissue of the patient. FIGS. 2–4 illustrate this sequence of the blunt tip distal end 32 being urged forwardly beyond the sharpened distal end 54 as the distal spring force applied by the large spring 20 overcomes the smaller proximal spring force of the smaller spring 22. At this point, the user attaches a luer tip syringe (not shown) to an adapter 62 provided at the proximal end of thoracentesis device 10 by inserting the tip of the syringe through proximal opening 86 and into passage 60 until a sealing engagement with proximal opening 86 is achieved. The user then pulls the plunger of the syringe backward in order to create a negative pressure within the pleural cavity 45 that suctions fluid into the plurality of radial ports 36 of inner needle 28. The suctioned fluid is then evacuated through the conduit 34 and out valve 26 where it enters the body of the syringe.

As noted above, the present invention contemplates a hypersensitive detection means for detecting any resistance met by the blunt tip distal end 32. During thoracentesis or any similar medical procedure the user must manipulate the distal end of thoracentesis device 10 within the pleural cavity 45 in order to effectively suction secretions throughout cavity 45. However, such manipulation of the thoracentesis device 10 may cause inadvertent contact with the lungs 43 or other sensitive internal body organ. As shown in FIGS. 6 and 7, inadvertent contact of the blunt tip distal end 32 with the lungs 43 causes end 32 to be forced backward. As the inner needle 28 is driven backward into conduit 34 the small spring 22 exerts a proximal spring force in the same direction, which in combination with a resistive force A generated by the contacted organ, moves the positive indicator 16 relative to negative indicator 18 and unmask negative indicator 18 from its hidden nesting position within positive indicator 16. As the negative indicator 18 comes into view it visually alerts the user that blunt tip distal end 32 has made contact with a body organ.

Figure 8:
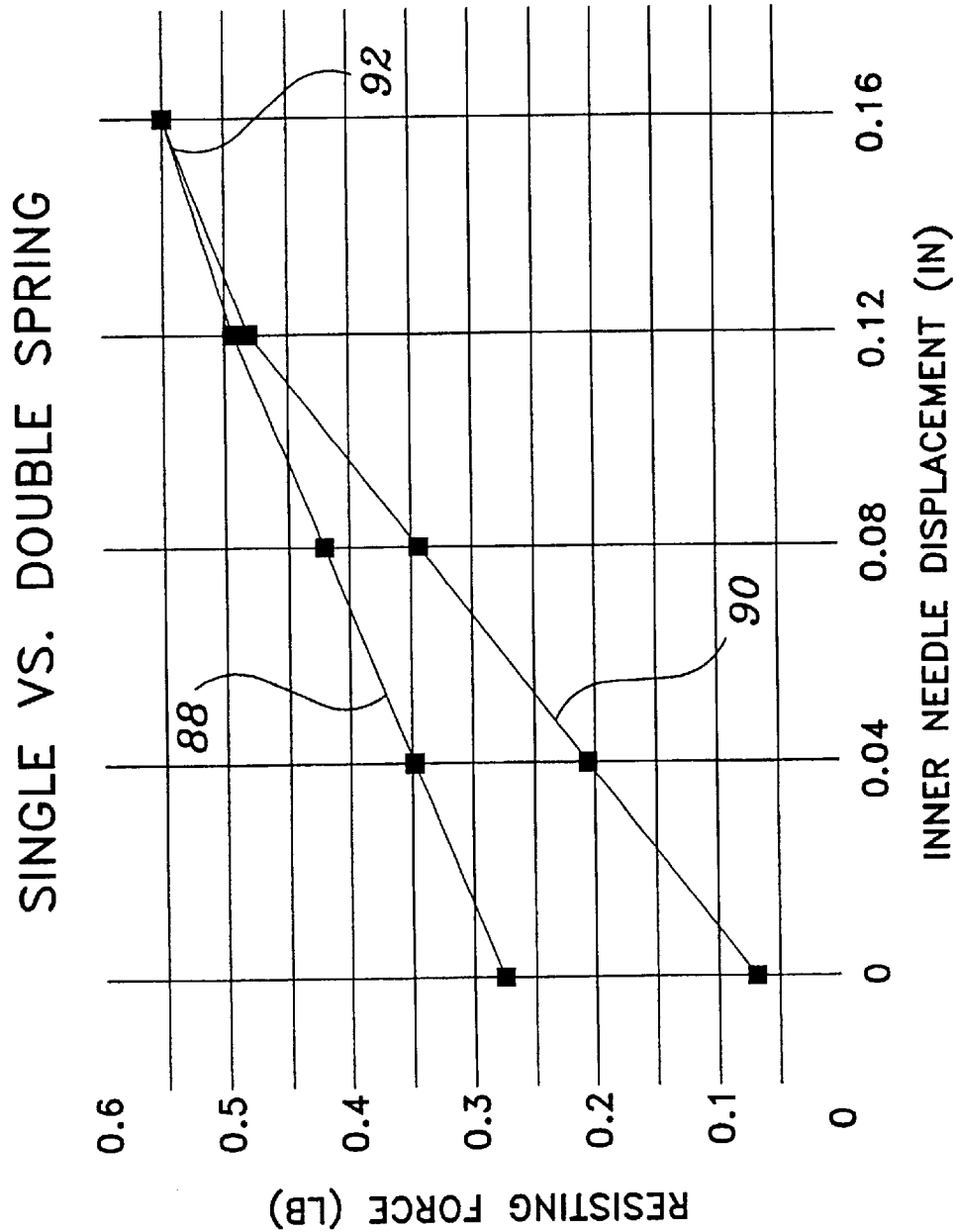
FIG. 8 is a graph illustrating the enhanced sensitivity of the dual spring arrangement according to the present invention relative to the prior art single spring arrangement.

Referring to FIG. 8, a graph is shown illustrating the greater detection sensitivity of the dual spring arrangement 90 according to the present invention in comparison to the single spring arrangement 88 of prior art detection mechanisms. As shown in FIG. 8, it takes a much smaller resisting force being generated by the contacted internal body organ in order to displace the inner needle 28 and unmask the negative indicator 18, thereby more quickly alerting the user. For example, inner needle 28 of the present invention begins to displace the positive indicator 16 and unmask negative indicator 18 when 0.075 lbs. of combined force generated by both the resistance of the lung 43 and the proximal spring force of small spring 22 are applied to inner needle 28. In contrast, it takes at least 0.275 lbs. of resistive force alone to begin displacing the inner needle of the prior art single spring arrangement. It is not until over 0.55 lbs. of force has been applied that both the double spring arrangement and single spring arrangement have equal displacement of the positive indicator 16 for the same force as noted at point 92.

It can be appreciated that the double spring arrangement of the present invention promotes enhanced detection sensitivity and quicker visual indication of detection to the user due to the addition of a small spring 22 to the double spring arrangement. Accordingly, the combined resisting force and proximal spring force applied by the small spring 22 in direct opposition to the larger distal spring force applied by the large spring 20 permits a more rapid displacement of positive indicator 16 since the spring force of the small spring 22 supplements the resisting force of the contacted organ in overcoming the distal spring force of the large spring 20. Preferably, both large and small springs 20, 22 are made from any suitable flexible metal, however any resilient, flexible material that imparts a spring force upon compression is felt to fall within the scope of the present invention. The present invention contemplates that positive and negative indicators may have any contrasting colors, such as red and green, which will visually alert the user. It should be apparent to those skilled in the art that the present invention, although intended for thoracentesis, could also be applied to similar medical procedures, such as paracentesis, pneumothorax, or pericardiocentesis that require some type of hypersensitive detection mechanism to prevent laceration or puncture of internal body organs.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

I/we claim:

1. A medical device for removing fluid from a cavity comprising:
    a body;
    a spring-loaded needle slidably disposed within said body;
    a first spring housed in said body and associated with said needle, said first spring having a first spring force for urging said needle in one direction; and
    a second spring having a second spring force being applied to said needle in an opposite direction to said first spring force of said first spring.

2. The medical device according to claim 1, wherein said medical device further includes another needle, said needle defining a conduit.

3. The medical device according to claim 2, wherein said needle is slidably disposed inside said conduit.

4. The medical device according to claim 1, wherein said body is transparent.

5. The medical device according to claim 4, wherein said medical device further comprises a first indicator associated with said needle, said first indicator giving a visual indication that said needle is in the fully extended position.

6. The medical device according to claim 4, wherein said medical device further comprises a second indicator associated with said first indicator, said second indicator giving a visual indication that said needle is not in the fully extended position.

7. The medical device according to claim 6, wherein said second indicator is nested inside said first indicator.

8. The medical device according to claim 6, wherein said second indicator is fully hidden from view when said needle is in the fully extended position.

9. The medical device according to claim 6, wherein said first indicator is not fully hidden from view when said needle in not is the fully extended position.

10. The medical device according to claim 9, wherein said needle extends farther from said housing than said needle when said needle is in the fully extended position.

11. The medical device according to claim 1, wherein said first spring force is greater than said second spring force.

12. The medical device according to claim 1, wherein said needle includes a blunt tip.

13. The medical device according to claim 1, wherein said body includes a front housing and a rear housing threadably connected to said front housing.

14. The medical device according to claim 1, wherein said thoracentesis devise further comprises a one way valve disposed in a cavity of said body.

15. The medical device according to claim 1, wherein said body includes an opening for the evacuation of fluid from said body.

16. A medical device for removing fluid from a cavity comprising:

a housing;

a needle slidably disposed within said housing;

a positive indicator and a negative indicator disposed in said housing, said positive and negative indicators being operatively associated with said needle;

a large spring associated with said needle and disposed in said housing, said large spring providing a spring force for urging said needle to said fully extended position; and a small sprint disposed in said housing for applying a counter spring forge to said needle;

whereby said spring force and said counter spring force oppose one another.

17. The medical device according to claim 16, wherein said spring force of said large spring applies a greater axial force than said counter spring force of said small spring.

18. The medical device according to claim 17, wherein when said inner needle is not in the fully extended position said negative indicator is not hidden by said positive indicator.

19. The medical device according to claim 16, wherein said positive indicator gives a visual indication that said needle is in the fully extended position.

20. The medical device according to claim 16, wherein said negative indicator gives a visual indication that said needle is not in the fully extended position.

21. The medical device according to claim 16, wherein said negative indicator is normally nested and hidden inside said positive indicator.

22. The medical device according to claim 16, wherein the medical device further includes a needle, said needle being fixedly connected to said housing.

23. The medical device according to claim 16, wherein said needle is spring loaded.

* * * * *

UNITED STATES PATENT AND TRADEMARK OFFICE
CERTIFICATE OF CORRECTION

PATENT NO. : 6,638,251 B2
DATED : October 28, 2003
INVENTOR(S) : Gregory Alan Steube et al.

It is certified that error appears in the above-identified patent and that said Letters Patent is hereby corrected as shown below:

Title page,
Item [75], Inventors should read:-- Gregory Alan Steube, St. Charles, MO (US); Alan Ranford, Creve Couer, MO (UK); Ronald Lloyd, Deland, FL (UK). --

Column 9,
Line 3, change "in not is the fully extended position" to -- is not in the fully extended position --.

Column 10,
Line 12, change "a small sprint disposed in said housing for applying a" to -- a small spring disposed in said housing for applying a --.

Signed and Sealed this

Fourth Day of May, 2004

JON W. DUDAS
*Acting Director of the United States Patent and Trademark Office*